US00PP08155P

United States Patent [19]

Austin

[11] Patent Number: Plant 8,155

[45] Date of Patent: Feb. 23, 1993

[54] ROSE PLANT — 'AUSREN'

[75] Inventor: David C. H. Austin, Albrighton, England

[73] Assignee: David Austin Roses, Wolverhampton, England

[21] Appl. No.: 623,305

[22] Filed: Dec. 6, 1990

[51] Int. Cl.[5] ..... A01H 5/00

[52] U.S. Cl. ..... Plt./1

[58] Field of Search ..... Plt./1, 22, 26, 27

*Primary Examiner*—Howard J. Locker

*Attorney, Agent, or Firm*—Ladas & Parry

[57] ABSTRACT

A new variety of rose plant of the shrub class distinctive in its character by its fully double, lilac pink coloring with abundant continual blooming, and the unusual shaping of the flowers.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof. It is also noted that the usual and pleasing petal coloration intensified in color darkness with blossom, age and exposure.

BRIEF DESCRIPTION OF THE DRAWING

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of Colour" published by Eyre Methuen Ltd (1963).

Variety denomination (in accordance with the UPOV Convention): Ausren.

*Cultivar trade name.*—Charles Rennie Mackintosh.

*Type.*—Hardy, bushy, outdoor, seedling, garden decoration.

*Class.*—Shrub.

Propagation: This variety holds its distinguishing characteristics through succeeding propagations by budding.

Asexual reproduction of the new cultivar by budding has taken place at a nursery in Albrighton, Nr. Wolverhampton, England and was derived as follows Female parent (seed parent): Chauser×Conrad F. Meyer (both non-patented).

Male parent (pollen parent): Mary Rose (non-patented).

The operation of the artificial pollination is therefore expressed by the following (Chauser×Conrad F. Meyer)×Mary Rose.

The following observations are made of specimens grown outdoors in England.

PLANT DESCRIPTION

Plant:

Height.—110 cm.

*Habit.*—Bushy, and strong.

Branches:

Young stems.—Color: Greyish green 28D6. Texture: Smooth and glabrous. Thorns: 6–10 per node reddish brown 9D5/6 and numerous red glandular hairs on older nodes.

*Old stems.*—Color: 30E8 Parrot Green. Texture: Smooth. Thorns: 4–6 per node. 2A7/5 pale yellow deepening to brown 7E7/8 at apex.

LEAVES

Stipules:

*Length.*—About 25 mm.

*Width.*—Max. 6–8 mm.

*Angle of wingtips to petiole.*—Less than 45°.

*Color.*—30D8.

*Margins.*—Lined with red tipped glandular hairs, wings convex and somewhat clasping at base.

*Shape.*—Broadly winged.

Petiole:

*General description.*—Length: About 70 mm (Mature leaves). Upperside color: Deep green 29E8. Groove/hairs/thorns: Sparse red tipped hairs at edge of the groove. Underside: 29D7 Greyish green. Hair/thorns: Sparse red tipped glandular hairs. Thorns, 1–3 per node, pale yellow 2A3 deeping to reddish brown 10C8 at apex.

Leaflets:

*Number.*—5–7.

*Shape.*—Ovate with cordate base and cuspidate apex.

*Serration.*—Dentate.

*Texture.*—Leathery, semi-dull.

General effect of foliage: Medium density; medium green.

Color:

*Young foliage.*—Upperside: 29E7 Broken green. Reddish brown mid rib and margin. Underside: 29E6/7 Greyish green. Reddish brown margins.

*Adult foliage.*—Upperside: 28F8 Dark green. Underside: 29E5/6 Greyish green.

INFLORESCENCE

Number of flowers per stem: 1, 4, 5 (mainly 4).

Peduncle:

*Length.*—40–50 mm.

*Color.*—28D8 Deep green.

*Thorns/hairs.*—Medium dense red glandular hairs.

Sepals:

*Upperside color.*—28D8 Deep green with red glandular hairs.

*Outer margins.*—With red glandular hairs and ensiform protrusions. Apex extended into an ensiform protrusion.

*Inner margins.*—Densely tomentose.

*Underside color.*—29C7 Apple green.

*Texture.*—Densely tomentose.

*Sepal length.*—20–25 mm.

Bud:

*Shape.*—Round with flattened base. Cuspidate apex drawn out into leaf-like ensiform protrusions.

*Length.*—30 mm.

*Max. width.*—12 mm.

*Color when opening.*—11C8 Deep red.

Flower:

*Shape.*—As a flattened cup. Top flat. Base rounded, cordate.

*Diameter.*—65–70 mm when blooming.

*Color when opening.*—Upperside: Outer and inner petals: Base 3A6 yellow, changing to 12A4 rose. Underside: Outer and inner petals: Base 2A5 sunshine, changing to 12A2/3 pinkish white/-pale red.

*Color when blooming.*—Upperside: Base 3A5 light yellow changing to 12A2/3 pinkish white/pale red. Underside: Base 2A4 pastel yellow changing to 12A2 pinkish white.

*Coloring when finished blooming.*—Upperside: Outer and inner petals: Base 2A3/4 pale yellow/pastel yellow changing to 13A2 pinkish white. Underside: Outer and inner petals: Base 2A3 pale yellow changing to 14A2 purplish white.

Length of blooming season at production location: From June To October.

Fragrance: None.

Lasting quality: Very good. Range in number of days on plant is 10–12. Range in number of days as cut flowers is 7–10.

Petals:

*Shape.*—Outside: Cupped (i.e. not flat), rounded with bilobed apex and cuneate base. Middle: Somewhat cupped, elongated heart shape with bilobed apex and acute base. Inside: Somewhat cupped, elongated heart shape. Apex of petals caught into center of receptacle. Acute base.

*Texture.*—Soft.

*Number.*—150–160.

*Cleaning.*—Medium, the petals fall reasonably quickly but not as quickly as they should do.

Stamens:

*Number.*—20–25.

*Anthers.*—Normal golden yellow 3A8.

*Filaments.*—Irregular heights, pale yellow 3A4.

Pistils:

*Number.*—About 60.

*Stigmas.*—4A8.

*Styles.*—Straw 3A4 colored at base top irregular height.

Receptacle:

*Color.*—29D7 greyish green.

*Texture.*—Smooth.

*Size.*—Length 8–10 mm. Max width 8–10 mm.

*Shape.*—V-shaped.

THE DEVELOPMENT

Vegetation: Vigorous.

Blooming: Abundant and continual.

Aptitude to bearing fruits: None.

Resistance to frost: Very good.

Resistance to disease: Very good.

I claim:

1. A new and distinct variety of rose plant of the shrub class, characterized as to novelty by its fully double flowers giving the effect of lilac pink coloring, with abundant and continual blooming and shaping of the flower being substantially as shown and described.

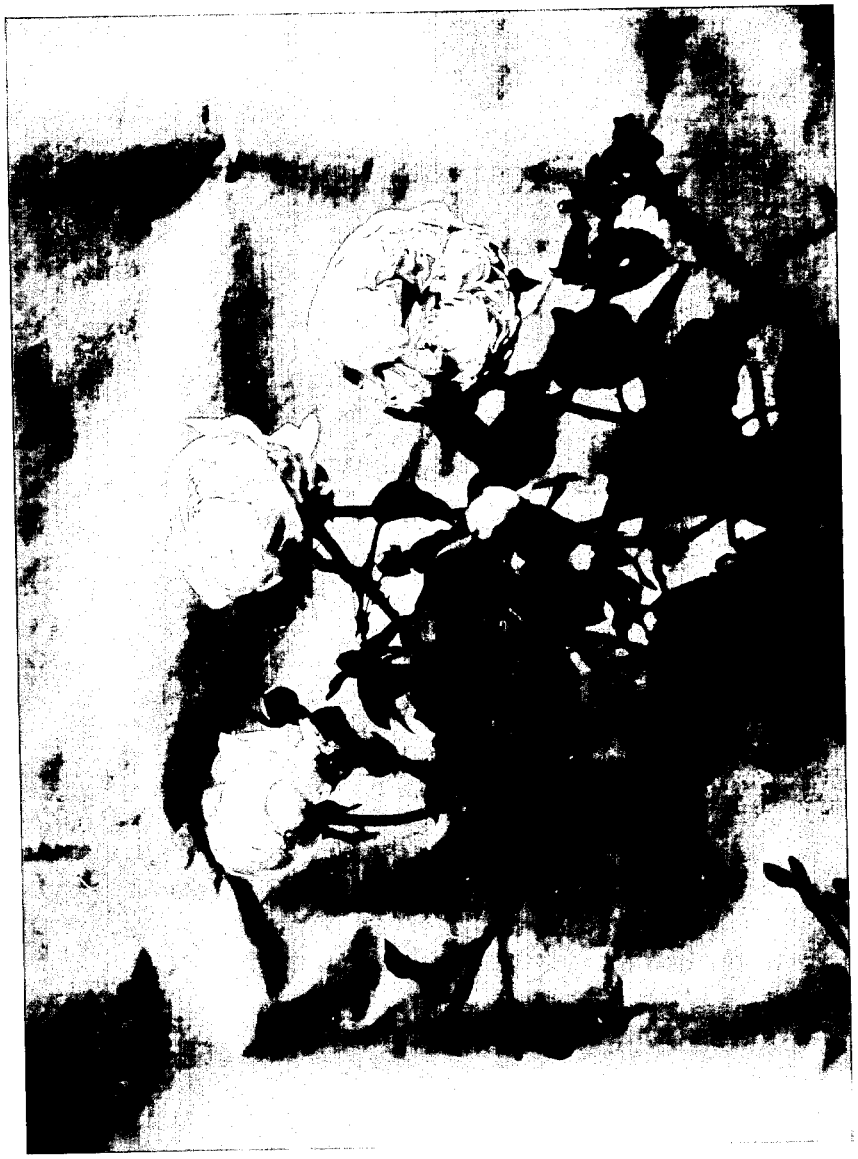

* * * * *